(12) United States Patent
Quaye

(10) Patent No.: US 10,010,246 B2
(45) Date of Patent: Jul. 3, 2018

(54) STEERABLE ENDOSCOPES

(71) Applicant: Roland Quaye, Fredericksburg, VA (US)

(72) Inventor: Roland Quaye, Fredericksburg, VA (US)

( * ) Notice: Subject to any disclaimer, the term of this patent is extended or adjusted under 35 U.S.C. 154(b) by 140 days.

(21) Appl. No.: 15/167,468

(22) Filed: May 27, 2016

(65) Prior Publication Data
US 2017/0181603 A1    Jun. 29, 2017

Related U.S. Application Data

(60) Provisional application No. 62/167,853, filed on May 28, 2015.

(51) Int. Cl.
*A61B 1/00* (2006.01)
*A61B 1/005* (2006.01)
*A61B 1/05* (2006.01)

(52) U.S. Cl.
CPC .......... *A61B 1/0056* (2013.01); *A61B 1/0057* (2013.01); *A61B 1/05* (2013.01)

(58) Field of Classification Search
CPC ............................... A61B 1/0057; A61B 1/01
USPC ........................................ 600/123, 141, 146
See application file for complete search history.

(56) References Cited

U.S. PATENT DOCUMENTS

| | | | |
|---|---|---|---|
| 6,761,685 B2 * | 7/2004 | Adams | A61B 1/00073 600/121 |
| 6,875,170 B2 * | 4/2005 | Francois | A61B 1/0053 600/141 |
| 7,566,300 B2 * | 7/2009 | Devierre | A61B 1/00087 600/104 |
| 8,550,989 B2 * | 10/2013 | Dohi | A61B 1/00078 600/114 |
| 2007/0197862 A1 * | 8/2007 | Deviere | A61B 1/00087 600/102 |
| 2010/0133320 A1 * | 6/2010 | Bilotti | A61B 1/0014 227/176.1 |
| 2015/0359416 A1 * | 12/2015 | Simchony | A61B 1/0055 600/562 |

\* cited by examiner

*Primary Examiner* — Matthew J Kasztejna
(74) *Attorney, Agent, or Firm* — Mohr Intellectual Property Law Solutions, P.C.

(57) ABSTRACT

In one embodiment an apparatus for insertion in a body cavity (e.g., an endoscope) may include an elongate assembly, an instrument tip disposed at a distal end of the elongate assembly, and a terminal base disposed at a proximal end of the elongate assembly. The elongate assembly may include a first peripheral tube, a second peripheral tube spaced apart from the first peripheral tube and a plurality of collar members. Each collar member may include a first channel grasping the first peripheral tube, and a second channel grasping the second peripheral tube. The collar members may be spaced apart from one another along a length of the elongate assembly such that adjacent collar members do not contact one another. The terminal base may include a first control fitting attached to the first peripheral tube and a second control fitting attached to the second peripheral tube. The first control fitting may be configured to apply tension to the first peripheral tube. The second control fitting may be configured to apply tension to the second peripheral tube.

14 Claims, 5 Drawing Sheets

STEERABLE ENDOSCOPES

CROSS REFERENCE TO RELATED APPLICATIONS

This application claims priority to U.S. Provisional Patent Application, Ser. No. 62/167,853, filed on May 28, 2015, which is hereby incorporated by reference for all purposes.

BACKGROUND

The present disclosure relates generally to endoscopes. In particular, steerable endoscopes manipulated by tension applied on one or more tubes of the endoscope are described.

Endoscopes are used in medical procedures to examine the interior of a hollow organ or cavity of the body. Endoscopes generally include a camera, a light source, and a steering mechanism to perform internal imaging of a patient.

Known endoscopes are not entirely satisfactory for the range of applications in which they are employed. For example, existing endoscopes may be overly bulky and uncomfortable for the patient during use, particularly when used for endoscopy in smaller organs and bodily cavities (e.g., rhinoscopy, bronchoscopy, cystoscopy, etc.). In addition, conventional endoscopes may be disruptive to the patient's internal organs and/or fluids within the organs during use. Further, re-use of endoscopes between different patients can cause cross contamination and/or spread of hospital acquired disease.

Thus, there exists a need for endoscopes that improve upon and advance the design of known endoscopes. Examples of new and useful endoscopes relevant to the needs existing in the field are discussed below.

SUMMARY

In one embodiment an apparatus for insertion in a body cavity (e.g., an endoscope) may comprise an elongate assembly, an instrument tip disposed at a distal end of the elongate assembly, and a terminal base disposed at a proximal end of the elongate assembly. The elongate assembly may comprise a first peripheral tube, a second peripheral tube spaced apart from the first peripheral tube and a plurality of collar members. Each collar member may comprise a first channel grasping the first peripheral tube, and a second channel grasping the second peripheral tube. The collar members may be spaced apart from one another along a length of the elongate assembly such that adjacent collar members do not contact one another. The terminal base may comprise a first control fitting attached to the first peripheral tube and a second control fitting attached to the second peripheral tube. The first control fitting may be configured to apply tension to the first peripheral tube. The second control fitting may be configured to apply tension to the second peripheral tube.

DETAILED DESCRIPTION

The disclosed steerable endoscopes will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of steerable endoscope examples are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Figure 1:
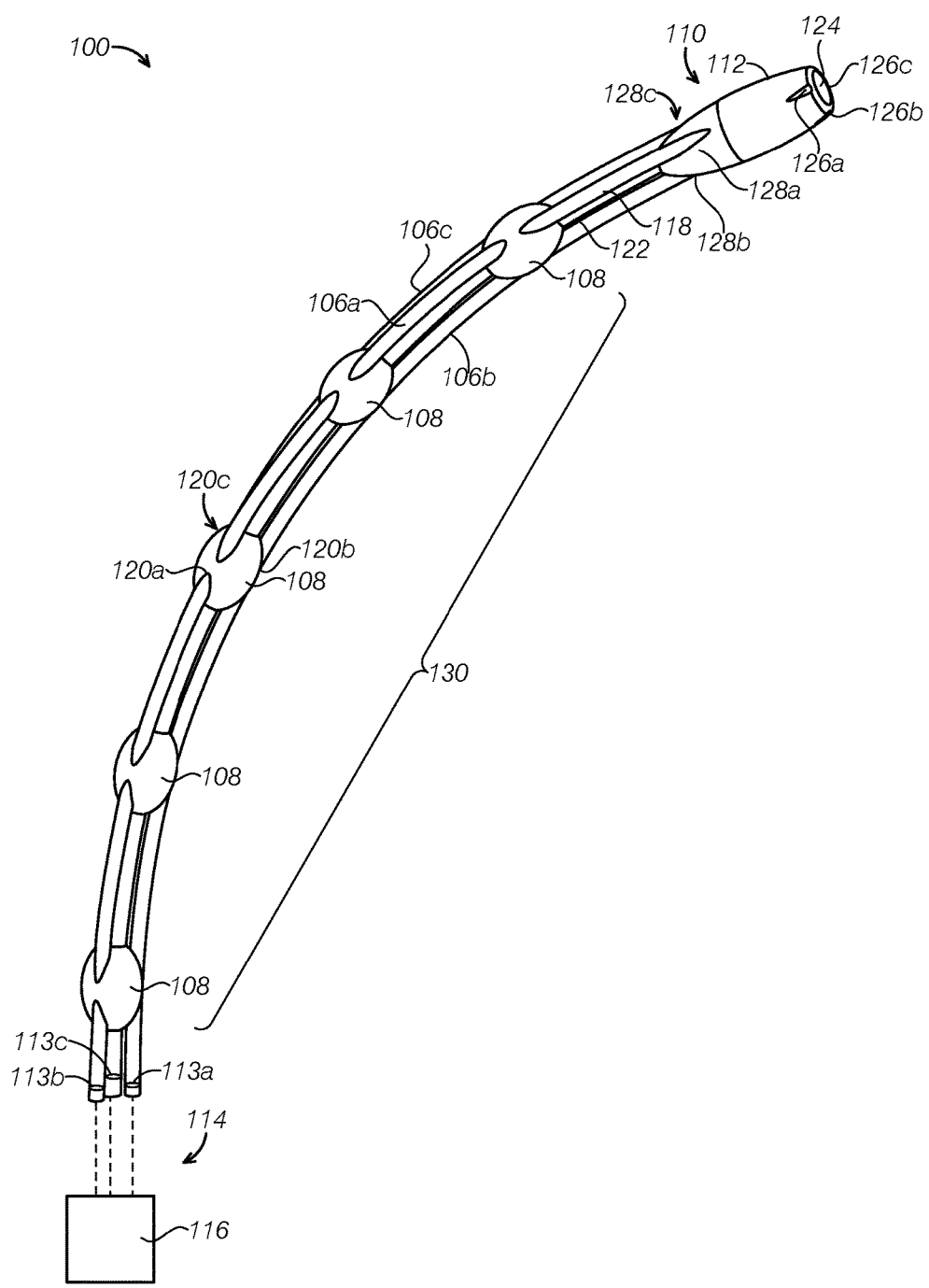
FIG. 1 is a side view of a first embodiment of a steerable endoscope in a flexed position.
Figure 2:
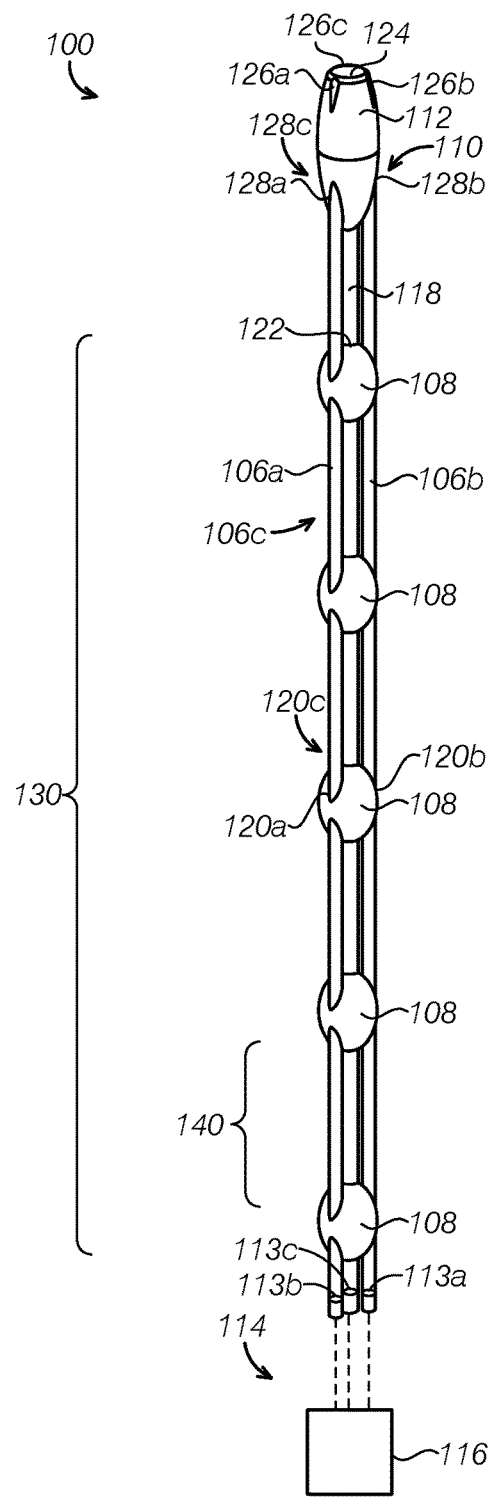
FIG. 2 is a side view of the steerable endoscope of FIG. 1, shown in an un-flexed position.
Figure 3:
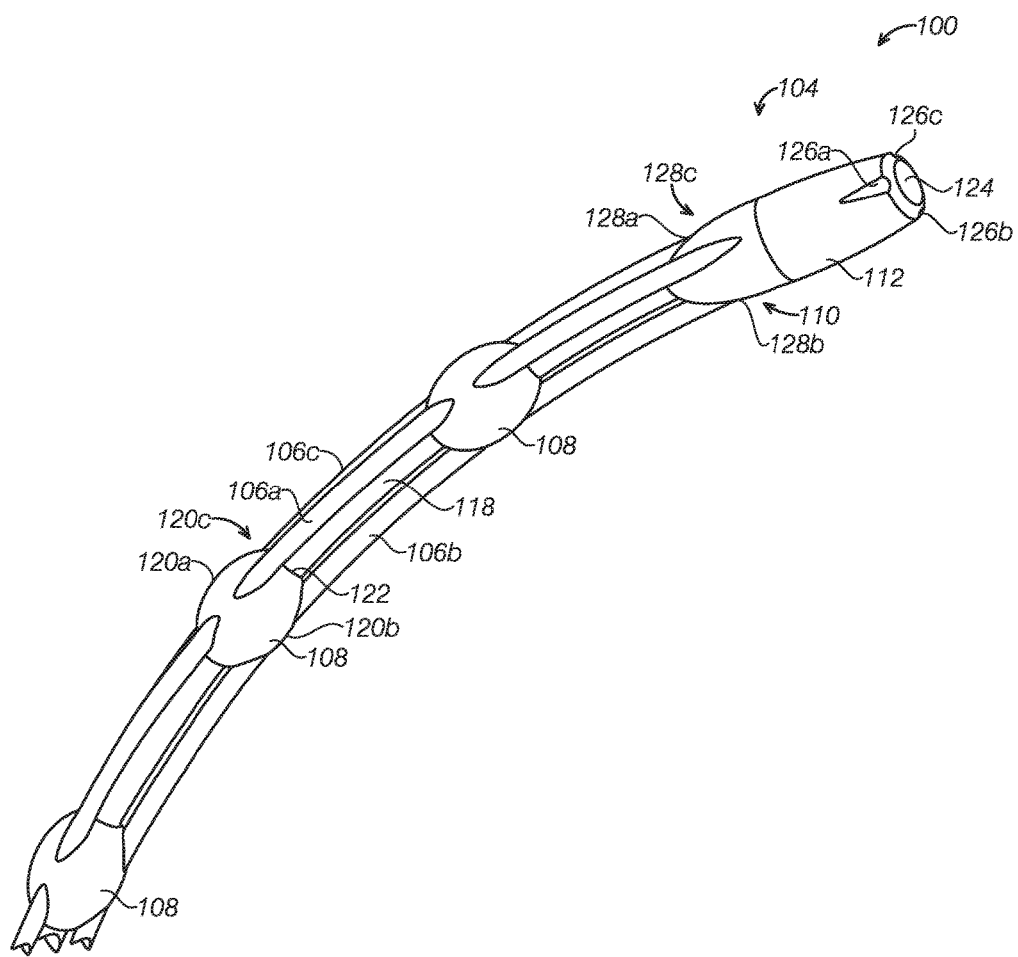
FIG. 3 is a side view of the distal tip of the first embodiment of the endoscope.
Figure 4:
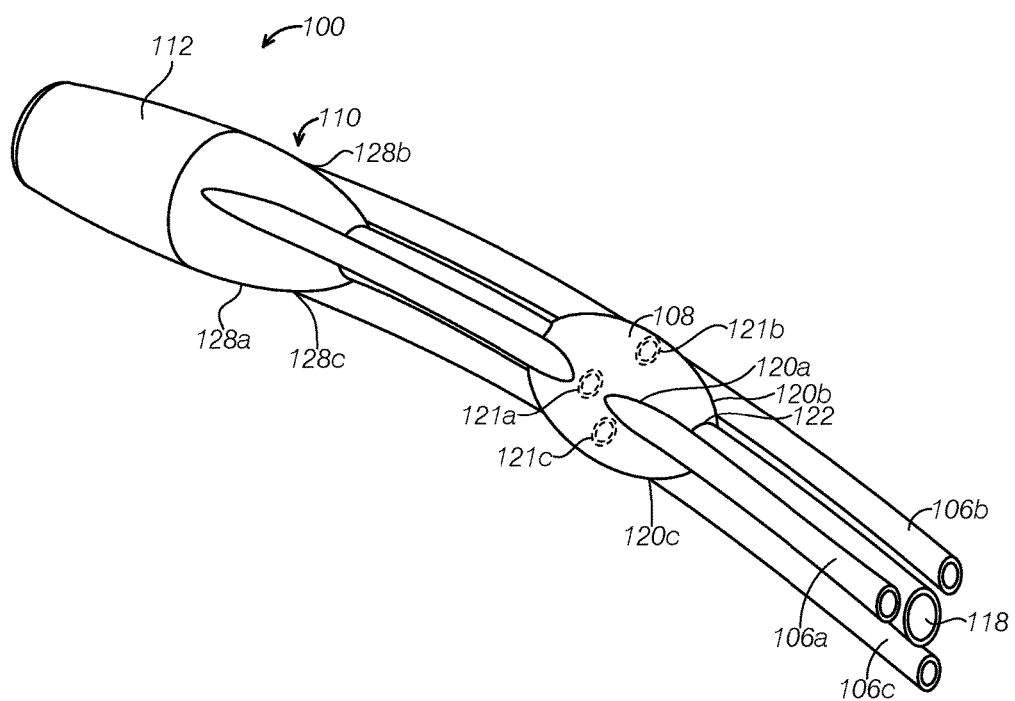
FIG. 4 is a rear view of the distal tip of the first embodiment of the endoscope.

With reference to FIG. 1 a first example of a steerable endoscope, endoscope 100, will now be described. Endoscope 100 is insertable into an organ or a body cavity for viewing and/or examining the interior of the organ or cavity and includes a plurality of peripheral tubes bundled together by collar members 108. Endoscope 100 is steerable to navigate to a specific organ or body cavity or a specific location within the organ or body cavity by applying tension to one or more tubes of the endoscope. Additionally or alternatively, the tubes can be used to transport or deliver air, water, medicine, suction, light, surgical tools, power, etc. Additionally or alternatively, endoscope 100 can be disposable.

Endoscope 100 addresses many of the shortcomings existing with conventional endoscopes. For example, the peripheral tubes of the endoscope are configured for both directing and/or delivery of air, water, medicine, suction, light, surgical tools, power, etc. as well as steering of the endoscope. This allows for the endoscope to have a narrow width that can be more comfortable for the patient and/or usable within smaller body cavities and/or organs (e.g., rhinoscopy, bronchoscopy, cystoscopy, etc.). Further, endoscope 100 allows bodily fluids to move between the peripheral tubes of the endoscope, thereby preventing blockage of blood vessels and other bodily pathways. Furthermore, endoscope 100 can be disposed of after use, thereby preventing cross contamination with other patients.

Referring now to FIG. 1, endoscope 100 includes an elongate assembly 130, an instrument tip 110 disposed at the distal end of the elongate assembly 130, and a terminal base 114 at the proximal end of the elongate assembly 130. The elongate assembly 130 may include a plurality of (e.g., three) peripheral tubes 106a-c banded together via a plurality of collar members 108.

Each of the plurality of collar members 108 may include several channels (e.g., three channels 120a-c). As used herein a channel means a void or socket in a collar member configured to grasp a tube. While the channels depicted in FIGS. 1-5 completely envelop the circumference of the tubes, in other embodiments, the channels may be partially open and envelop only a majority of the circumference of the tubes. In some embodiments, the channels 120 may be proximal to an outer perimeter of the collar member 108. Each channel 120 may be configured to grasp one of peripheral tubes 106. Specifically, channel 120a may be configured to grasp peripheral tube 106a, channel 120b may be configured to grasp peripheral tube 106b, and channel 120c may be configured to grasp peripheral tube 106c. Tubes 106a-c may each have the same diameter or they may have different diameters. The diameters of channels 120a-c may be configured to compliment the diameter(s) of peripheral tubes 106a-c.

In one embodiment, the elongate assembly may be assembled by forcibly sliding peripheral tubes 106a-c through the channels 120a-c of a first collar member 108, then repeating the process for the next collar member 108 until the elongate assembly is complete. In some embodiments, channels 120 may be sized to grasp the peripheral 106 tubes via friction. In other embodiments, the channels 120 may be fixedly attached to the peripheral tubes 106 via an adhesive.

Additionally or alternatively, one or more of the peripheral tubes may include a plurality of projections 121a-c extending from the exterior surface of the tube to slidably secure the collar members 108. In one embodiment, the projections 121a-c may comprise annular rings. In some embodiments, one or more of the channels 120a-c may comprise a receiving space to receive and/or at least partially surround the projections. In this regard, the projections 121a-c and receiving spaces may serve to secure the collar members from sliding on the peripheral tubes 106.

Endoscope 100 may be flexed in different directions by applying tension to the proximate end of one or more of the peripheral tubes. For example, as shown in FIG. 1, applying tension to the proximate end of the right-most peripheral tube 106b may cause the elongate assembly 130 to bend to the right. As may appreciated, the endoscope can be alternatively flexed in other directions by applying tension to the proximate end of one or more of the other peripheral tubes 106a, 106c.

Collar members 108 may serve to bundle peripheral tubes 106 together. In this regard, peripheral tubes 106 may be held essentially parallel to each other as the elongate assembly 130 is controllably flexed. In some embodiments having three peripheral tubes 106, collar members 108 may hold peripheral tubes essentially equidistant from each other as the elongate assembly 130 is flexed. As shown in FIGS. 1-4 collar members 108 maintain the spacing between the peripheral tubes 106. Thus, in some embodiments, the peripheral tubes form an open chase running the length of the elongate assembly 130. This open chase may allow bodily fluids to pass through and/or around the endoscope 100. In other embodiments, the elongate assembly may be encased in a flexible outer tube (not pictured).

Collar members 108 may be spaced apart from each other along the elongate assembly 130. In some embodiments collar members 108 may be spaced apart from each other in regular intervals. For example, in one embodiment, collar members 108 may be spaced apart from each other such that the distance between each collar member (e.g., the distance from the distal tip of one collar member to the proximal tip of the next) is approximately twice the length of one of the collar members 108. In other embodiments, the collar members may be spaced apart from each other such that the distance between a first collar member and its neighboring collar members is at least the length of the first collar member.

In other embodiments, the spacing between collar members 108 may be varied. In one example, the spacing between collar members may incrementally increase from the proximal end to the distal end of the endoscope. In another example, the spacing between collar members may incrementally decrease from the proximal end to the distal end of the endoscope.

In some embodiments, it may be important to ensure that the collar members to not contact each other as the endoscope is controllably flexed. In one embodiment, the collar members are spaced apart from each other such that when the elongate assembly is flexed up to 90 degrees, the collar members do not contact each other.

In the present example, the collar members 108 are comprised of a material with a higher degree of flexibility (e.g., silicone medical grade rubber or other rubbers such as PVC's with a lower Shore A hardness) and the peripheral tube 106 are comprised of a material with a lesser degree of flexibility (e.g., silicone medical grade rubber or other rubbers such as PVC's with a higher Shore A hardness). As tension is applied on one or more of the peripheral tubes while the other peripheral tubes remain in a relaxed state, the tube causes flex on the side of the collar member corresponding to the location of the tube. The tension is then relayed to downstream collar members and results in overall flex of the endoscope in a direction toward the one or more tubes on which the tension is applied.

Also shown in FIGS. 1-4, instrument tip 110 of endoscope 100 may include a housing 112. Housing 112 may comprise a camera 124. Housing 112 may include apertures 128 (e.g., 128a, 128b, and 128c). Each peripheral tube 106 may include an inner lumen. The inner lumens may be uninterrupted and fluid tight from the proximal end to the distal end of the elongate assembly 130. Each aperture 128 may be in fluid connection with an inner lumen of the peripheral tubes 106. For example, aperture 128a may be in fluid communication with the inner lumen of peripheral tube 106a, aperture 128b may be in fluid communication with the inner lumen of peripheral tube 106b, and/or aperture 128c may be in fluid communication with the inner lumen of peripheral tube 106c.

Each of the apertures 128 has an outer orifice 126 (i.e., 126a, 126b, and 126c). Accordingly, the inner lumens of the peripheral tubes 106 can direct and/or deliver air, water, medicine, suction, light, surgical tools, power, etc. from the proximal end to the distal end of the endoscope 100 and out through the orifice in the housing 112.

The terminal base 114 of endoscope 100 includes the proximal ends of peripheral tubes 106. Each of the proximal ends of the peripheral tubes 106 may be is coupled to a steering/tensioning mechanism 116 via a respective control fitting 113a-c. The control fitting 113 may comprise a ferrule having one or more annular rings. The ferrule may grip the inner and/or exterior surface of the proximal end of the peripheral tube 106. In this regard, the control fitting 113 may be configured to apply tension to the peripheral tube 106.

Steering of the endoscope 100 (such as through the method described above) can change a direction in which the housing 112 is pointed (e.g., for image capture, delivery through the tubes, etc.). Steering of the endoscope can additionally be used to navigate the endoscope 100 through the internal organ or body cavity.

In the present example, steering/tensioning mechanism 116 is schematically depicted. The steering/tensioning mechanism is attached to each of the peripheral tubes, via control fittings 113*a-c*, for alternatively and/or cooperatively applying tension (i.e., via pulling) on each of the tubes to bend and/or flex the endoscope in a desired direction, while one or more of the other tubes remains in a relaxed state. For example, the steering control mechanism may apply tension to the first peripheral tube via the first control fitting 113*a* to direct bending of the endoscope in first direction, and apply tension to the second peripheral tube via the second control fitting 113*b* to direct bending of the endoscope in a second direction.

Thus, in contrast to conventional endoscopic devices which may apply tension to cables within tubes to compress the tubes, the peripheral tubes of endoscope 100 are free of cables and the tubes themselves are placed under tension.

It will be appreciated that in alternate examples the endoscope can include more peripheral tubes for finer control of flex of the endoscope. It will be further appreciated that in other alternate examples the endoscope can include fewer tubes (e.g., for decreasing a width of the endoscope).

As shown in FIGS. 1-4, endoscope 100 may further include a central tube 118 disposed within the open chase formed by the peripheral tubes. Central tube 118 may be held in place via a central channel 122 of each collar member 108. In some embodiments, the central tube 118 can be comprised of a material with a relatively high degree of flexibility (e.g., silicone medical grade rubber or other rubbers such as PVC's with a higher Shore A hardness). The material of the central tube 118 may be the same or a different material than the material of the collar members 108. At the instrument tip of endoscope 100, central tube 118 is attached to housing 112. Central tube 118 can deliver power, light, and/or other controls for camera 124 housed within housing 112. In other examples, the central tube and central channels of the collar members can be excluded from the endoscope.

Figure 5:
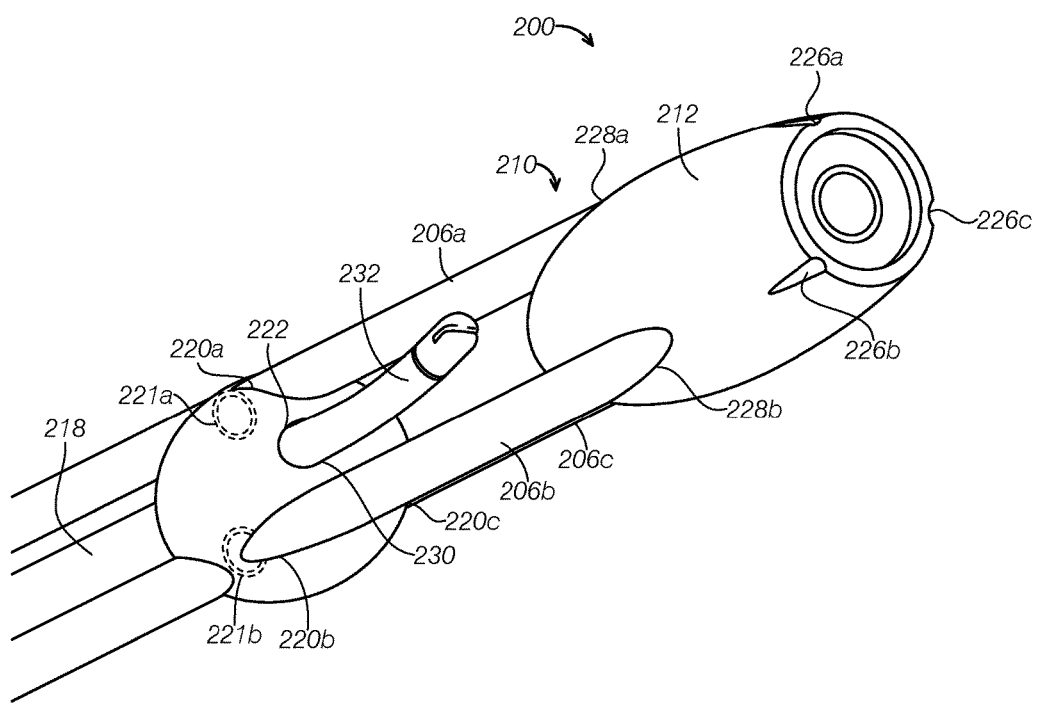
FIG. 5 is an isometric view of the distal tip of a second embodiment of a steerable endoscope.

Turning attention to FIG. 5, a second example of a steerable endoscope, endoscope 200, will now be described. Endoscope 200 includes many similar or identical features to endoscope 100. Thus, for the sake of brevity, each feature of endoscope 200 will not be redundantly explained. Rather, key distinctions between endoscope 200 and endoscope 100 will be described in detail and the reader should reference the discussion above for features substantially similar between the two steerable endoscopes.

As can be seen in FIG. 5, endoscope 200 includes peripheral tubes 206 (i.e., 206*a*, 206*b*, and 206*c*). Peripheral tubes 206 are joined at regular intervals by collar members 208. Each collar member 208 includes channels 220 (i.e., 220*a*, 220*b*, and 220*c*). Channels 220 may be proximal to an outer perimeter of the collar member 208. Each of channels 220 may grasp a peripheral tube 206.

In one example, each of the peripheral tubes 206 is fixedly attached within each of the channels. In some examples, the tubes 206 include projections 221*a-c* (e.g., annular ring projections, tabs, etc.) along the length of the tube that can be fitted into complimentarily configured receiving spaces (e.g., depressions, grooves, etc.) within the channels 220. In other examples, the peripheral tubes can be attached in the channels with an adhesive.

In the present example, the collar members are comprised of a material with a higher degree of flexibility (e.g., silicone medical grade rubber or other rubbers such as PVC's with a lower Shore A hardness) and the peripheral tubes are comprised of a material with a lesser degree of flexibility (e.g., silicone medical grade rubber or other rubbers such as PVC's with a higher Shore A hardness). As tension is applied on one or more of the peripheral tubes while the other peripheral tubes remain in a relaxed state, the tube causes flex on the side of the collar member corresponding to the location of the tube. The tension is then relayed to downstream collar members and results in overall flex of the endoscope in a direction toward the one or more tubes on which the tension is applied. It will be appreciated that although endoscope 200 is not specifically shown in flexed and non-flexed positions, endoscope 200 is movable between flexed and non-flexed positions, such as those depicted in FIGS. 1 and 2.

Also shown in FIG. 5, an instrument tip 210 of endoscope 200 includes a housing 212, which houses a camera 224. Housing 212 includes channels 228 (i.e., 228*a*, 228*b*, and 228*c*) that are continuous with tubes 206 (continuous with tubes 206*a*, 206*b*, and 206*c*, respectively). Further, tubes 206 are fixedly attached to housing 212. Each of channels 228 has an outer orifice 226 (i.e., 226*a*, 226*b*, and 226*c*). Accordingly, the tubes can direct and/or deliver air, water, medicine, suction, light, surgical tools, power, etc. through the tube and the channel and the orifice in the camera housing.

Although not specifically depicted, a terminal base of endoscope 200 is coupled to a steering/tensioning mechanism for changing a direction in which the camera housing pointed (e.g., for image capture, delivery through the tubes, etc.) and/or steering of the endoscope to navigate through the internal organ or body cavity. It will be appreciated that the steering/tensioning mechanism can be any desired steering/tensioning mechanism. The steering/tensioning mechanism is attached to each of the peripheral tubes for alternatively and/or cooperatively applying tension (i.e., via pulling) on each of the tubes to bend and/or flex the endoscope in a desired direction, while one or more of the other tubes remains in a relaxed state. It will be appreciated that in alternate examples the endoscope can include more peripheral tubes for finer control of flex of the endoscope. It will be further appreciated that in other alternate examples the endoscope can include fewer tubes (e.g., for decreasing a width of the endoscope).

Endoscope 200 further includes a central tube 218 disposed within a central channel 222 of each collar member 208. In the present example, the central tube can be comprised of a higher degree of flexibility material (e.g., silicone medical grade rubber or other rubbers such as PVC's with a lower Shore A hardness) that is the same or a different material than the material of the collar members. Differently from endoscope 100, at the instrument tip 210 of endoscope 200, central tube 218 is not attached to housing 212. Instead, central tube 218 stops at the last collar member 208 (i.e., collar member 208 immediately upstream of or before housing 212).

Thus, central channel 222 forms an orifice 230 at the last collar member 208. In this example, central tube 218 can enclose an endoscopic tool, such as endoscopic tool 232 depicted projecting through orifice 230 in FIGS. 6B and 7. In the present example, endoscopic tool 230 is a biopsy forceps device. In other examples, the endoscopic tool can be a vacuum device, a spray device, a surgical instrument, foreign body retrieval basket, a cauterization instrument, and/or one or more guide wire probes.

In some embodiments, the collar members 108, 208, each have a rounded shape. Specifically, the collar members may have a prolate spheroid shape. A longitudinal axis of the prolate spheroid shape is aligned with a longitudinal axis of the endoscope. The specific shape and configuration of the collar members contributes to smooth movement and sliding of the endoscope through the internal organ or body cavity. In alternate examples, the collar members can be ovoid or spherical in shape. Further, in alternate examples, the collar members can be disposed at irregular intervals along the length of the endoscope.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. An apparatus for insertion in a body cavity, the apparatus comprising: an elongate assembly comprising: a first peripheral tube; a second peripheral tube spaced apart from the first peripheral tube; a plurality of collar members, each collar member comprising: a first channel grasping the first peripheral tube; and a second channel grasping the second peripheral tube; wherein the collar members are spaced apart from one another along a length of the elongate assembly such that adjacent collar members do not contact one another; an instrument tip disposed at a distal end of the elongate assembly; and a terminal base disposed at a proximal end of the elongate assembly, the terminal base comprising: a first control fitting attached to the first peripheral tube, the first control fitting configured to apply tension to the first peripheral tube; and a second control fitting attached to the second peripheral tube, the second control fitting configured to apply tension to the second peripheral tube, comprising a steering control mechanism configured to: (i) apply tension to the first peripheral tube via the first control fitting to direct bending of the elongate assembly in first direction; and (ii) apply tension to the second peripheral tube via the second control fitting to direct bending of the elongate assembly in a second direction.

2. The apparatus of claim 1, comprising at least a third peripheral tube spaced apart from the first and second peripheral tubes such that the three peripheral tubes are essentially parallel and equidistant from one another, thereby forming an open chase surrounded by the three peripheral tubes.

3. The apparatus of claim 2, wherein each collar member includes a third channel grasping the third peripheral tube.

4. The apparatus of claim 2, comprising a central tube disposed in the open chase, wherein each of the plurality of collar members includes a central channel grasping the interior tube.

5. The apparatus of claim 4, comprising an endoscopic tool housed within the central tube.

6. The apparatus of claim 1, wherein the collar members are spaced apart from each other along the elongate assembly such that a distance between a first collar member and any neighboring collar members is at least the length of the first collar member.

7. The apparatus of claim 1, wherein the collar members are spaced apart from each other such that when the elongate assembly is flexed 90 degrees in a first direction, the collar members do not contact each other.

8. The apparatus of claim 1, wherein the first peripheral tube has an inner lumen, the lumen being uninterrupted and fluid tight from the proximal end to the distal end of the elongate assembly.

9. The apparatus of claim 1, wherein the instrument tip comprises a camera.

10. The apparatus of claim 1, wherein the collar members have an ellipsoid shape.

11. The apparatus of claim 1, wherein the collar members have a prolate spheroid shape.

12. The apparatus of claim 1, wherein the first peripheral tube has an exterior surface, the exterior surface including a plurality of projections extending therefrom, and wherein the first channel of each collar member includes a receiving space at least partially surrounding one of the plurality of projections.

13. The apparatus of claim 12, wherein the plurality of projections comprise annular rings.

14. The apparatus of claim 1, wherein the first control fitting comprises a ferrule configured to apply tension to the first peripheral tube; and the second control fitting comprises a ferrule configured to apply tension to the second peripheral tube.

* * * * *